United States Patent [19]

Hilerio et al.

[11] Patent Number: 5,098,849

[45] Date of Patent: * Mar. 24, 1992

[54] MATERIAL AND METHOD TO REDUCE NON-SPECIFIC BINDING OF A LABELLED MATERIAL

[75] Inventors: Fred J. Hilerio, San Jose; Stefan J. Kirchanski, Mountain View, both of Calif.

[73] Assignee: Becton Dickinson and Company, Franklin Lakes, N.J.

[*] Notice: The portion of the term of this patent subsequent to Mar. 31, 2004 has been disclaimed.

[21] Appl. No.: 218,712

[22] Filed: Jul. 13, 1988

[51] Int. Cl.[5] .................. G01N 33/566; G01N 33/53; C12Q 1/00
[52] U.S. Cl. ................................ 436/501; 252/408.1; 435/2; 435/7.1; 435/7.2; 435/7.21; 435/7.24; 435/7.25; 435/960; 435/962; 436/10; 436/17; 436/175; 436/579; 436/522; 436/546; 436/503; 436/825; 514/822
[58] Field of Search ............... 435/4, 7, 177, 2, 7.2, 435/7.21, 7.24, 7.25, 960, 962; 436/519, 520, 522, 824, 825, 10, 17, 175, 546, 501, 503; 252/408.1; 514/822

[56] References Cited

U.S. PATENT DOCUMENTS

| | | | |
|---|---|---|---|
| 3,826,364 | 7/1974 | Bonner et al. | 209/3 |
| 4,160,644 | 7/1979 | Ryan | 23/230 |
| 4,284,412 | 8/1981 | Hansen et al. | 23/230 |
| 4,520,110 | 5/1985 | Stryer et al. | 436/501 |
| 4,542,104 | 9/1985 | Stryer et al. | 436/536 |
| 4,654,312 | 3/1987 | Chang et al. | 436/519 |
| 4,661,913 | 4/1987 | Wu et al. | 364/500 |
| 4,755,379 | 7/1988 | Jozefonvicz et al. | 514/56 |
| 4,902,613 | 2/1990 | Chang et al. | 436/522 |
| 4,971,900 | 11/1990 | Ahnell et al. | 435/29 |

OTHER PUBLICATIONS

Herzenberg, et al., Sci. Am., 234:108 (1976).
The Merck Index 1983, p. 1025 entry 7001.

Primary Examiner—Robert A. Wax
Assistant Examiner—David R. Preston
Attorney, Agent, or Firm—Brian K. Stierwalt; Robert M. Hallenbeck

[57] ABSTRACT

A material and method are described to reduce the non-specific binding of a labelled material, wherein the labelled material comprises a fluorochrome and a specific binding pair member. The invention is particularlly suited to the lysis of peripheral blood wherein a labelled material is used to identify and detect cell populations within a sample of blood.

51 Claims, 3 Drawing Sheets

MATERIAL AND METHOD TO REDUCE NON-SPECIFIC BINDING OF A LABELLED MATERIAL

FIELD OF THE INVENTION

The present invention relates to a material and method to reduce non-specific binding of a labelled material, wherein the labelled material comprises a fluorochrome conjugated to a member of a specific binding pair. In its preferred embodiment, the present invention comprises an erythrocyte lysing solution which will reduce the non-specific binding of a labelled material. The present invention further relates to a method for reducing the non-specific binding of a labelling material.

BACKGROUND OF THE INVENTION

The ability to detect and quantify ligands and receptors (individually and collectively referred to as specific binding pair members) has become increasingly important. A variety of clinical conditions may be diagnosed and monitored by detecting the presence of and/or amount of a specific binding pair member in a sample. Examples of ligands which have a receptor includes compounds having either natural or synthetic activity. Such compounds may have low molecular weights (i.e., 125-2,000), such as small polypeptides, enzyme substrates, lipids and hormones, or may have higher molecular weights (i.e., >5,000), such as proteins, nucleic acids and glycoproteins. More specifically, such higher molecular weight compounds may include immunoglobulins and further may include monoclonal antibodies.

As the importance of measuring the presence of a specific binding pair member in a sample has increased, a number of means have been developed to detect such members. One method involves the direct conjugation of a label to the specific binding pair member. This labelled material then is allowed to tag the other specific binding pair member in a sample. The usefulness of the labelled material, however, will depend upon the specificity of the specific binding pair member for the other member, and also will depend upon the non-specific binding of the labelled material. The greater the non-specific binding of the labelled material, the lesser the sensitivity of the measurement will be.

Of great interest today is the use of fluorochromes as a label particularly when directly conjugated to monoclonal antibodies. When a fluorochrome is coupled to a monoclonal antibody the material may be used to label a cell bearing a specific receptor. The labelled material once bound to the specific receptor then may be detected by one of several means including a fluorescence light microscope and flow cytometer. U.S. Pat. No. 4,520,111 describes the conjugation of specific binding pair members to phycobiliproteins, and particularly to phycoerythrin (PE). U.S. Pat. No. 4,520,111 also describes the use of such labelled materials to tag lymphocytes and to be detected using flow cytometry. U.S. Pat. No. 4,542,104 further describes the conjugation of one or more fluorochromes to each other which then may be bound to a member of a specific binding pair.

In all of these cases, however, and in examples of conjugates not specifically described, the labelled material will bind non specifically. Depending upon the amount of non-specific staining, therefore, background fluorescence may cover up or mask the fluorescence signal from the labelled material specifically bound to the receptor. The degree of background or non-specific binding will limit the usefulness of the labelled material.

Non-specific binding does not appear to be a function of the method by which labelled material is prepared. Non-specific binding appears to result from the methods used to prepare the specific binding pair member to be detected (or material containing the member) prior to combining the labelled material with the member to be detected.

For example, in the preparation of whole blood lymphocytes for subset analyses by flow cytometry, erythrocytes are removed in order to leave a population of peripheral blood leukocytes (PBL). One method is to lyse the erythrocytes with a lysing solution. Such lysing solutions must be sufficiently strong to lyse the erythrocytes but must not be so strong to lyse the PBL. One solution that achieves these results is described in U.S. Pat. No. 4,654,312, and comprises an aqueous solution of a short chain (1-4) aliphatic aldehyde, an alkali or alkaline earth salt of a weak acid and a polyhydric alcohol.

The method of using this lysing solution generally comprises taking a sample of peripheral blood from an individual, adding a labelled material (e.g., anti-CD14 (PE)) to an aliquot of blood for a period of time sufficient to allow binding to the CD14 receptor, adding the lysing solution for a period of time sufficient to lyse the erythrocytes, centrifuging and washing the resulting mixture, adding a diluent to the mixture and placing the mixture into a flow cytometer. Modification to this method may include the addition of multiple labelled materials to the aliquot wherein, for example, each member binds to a different receptor and each fluorochrome has a different peak emission spectra, and/or the addition of dyes which differentially bind to nucleic acids. U.S. Pat. No. 4,654,312 describes one such method.

The limitation of this method, however, is that some non-specific binding will occur. As a result, a new method and material to reduce the non-specific binding of labelled material is needed.

SUMMARY OF THE INVENTION

In one embodiment of the invention, where the removal of erythrocytes is required, the present invention comprises a lysing solution that reduces the non-specific binding of a labelled material. The lysing solution comprises a short chain aliphatic aldehyde with a carbon chain of one to four, an alkali or alkaline earth metal salt of a weak acid, a polyhydric alcohol and one or more polyanions. More specifically, the salt may be selected from the group consisting of sodium and potassium salts of citrate, phosphate, acetate, formate, ascorbate and bicarbonate; the aldehyde may be selected from the group consisting of formaldehyde and butyraldehyde; and the polyhydric alcohol may be selected from the group consisting of glycerol, diethylene glycol and polyethylene glycol. Polyanions that may be used in the practice of this invention include sodium heparin, polyanethol sulfonate, pentosan polysulfate and chondroitin sulfate.

The present invention also comprises a labelled material that has reduced non-specific binding, wherein said labelled material comprises a label conjugated to a member of a specific binding pair to which one or more polyanions are added. More specifically, the labelled solution comprises a fluorochrome, such as a phycobiliprotein, conjugated to a monoclonal antibody to which one or more polyanions are added.

Finally, the present invention comprises a method for reducing the non-specific binding of a labelled material in a sample wherein the method comprises the steps of taking a sample from an individual, incubating an aliquot from such sample with a labelled material containing one or more polyanions to form a mixture for a time sufficient to allow binding of the labelled material to its other specific binding pair member and detecting fluorescence from the bound labelled material. Where the sample is blood, the method may be modified to include the step of adding an erythrocyte lysing solution containing one or more polyanions to the mixture. In this modified method, the labelled material need not contain polyanions.

Each of the several embodiments of this invention has the advantage over existing technologies in that non specific binding of the labelled material will be significantly reduced

DETAILED DESCRIPTION OF THE INVENTION

Figure 1A:
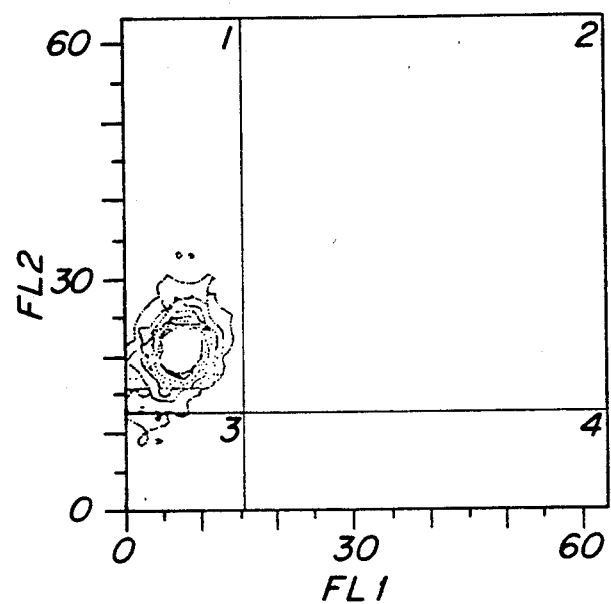
FIG. 1 comprises contour plots of fluorescence for PBL from a whole blood preparation tagged with Anti Leu M3(PE) using A) an erythrocyte lysing solution and B) an erythrocyte lysing solution to which heparin has been added.

The present invention generally comprises the use of polyanions to reduce the non-specific binding of labelled material. Polyanions may be added either to the labelled material directly or to a solution used to lyse erythrocytes. In either case, the binding of the labelled material to non target material will be reduced and as a result, the detection of specific binding will be improved. The sample may be taken from an individual and may comprise peripheral blood, urine, cerebral or spinal fluid or may comprise a cell suspension wherein the cells are isolated from spleen, liver, lymph node or bone marrow.

In one embodiment, where the sample comprises peripheral blood, one or more polyanions are added to an erythrocyte lysing solution. The improved lysing solution is added to an aliquot from a sample of blood to which a labelled material, preferably comprising a fluorochrome conjugated to a monoclonal antibody, has been previously added. After allowing sufficient time for the labelled material to tag its other specific binding pair member, the improved lysing solution is added to the aliquot. The resulting mixture is allowed sufficient time for the erythrocytes to lyse. The mixture then may be centrifuged and washed. The final material, which generally comprises a pellet of non-erythrocytes (or PBL), then may be prepared for detection of fluorescence.

Automated cell detection means, wherein the cells are examined in an area of focused optical stimulation substantially one at a time, such as a flow cytometer, then may be used to detect optical characteristics of the cells (e.g., fluorescence and/or light scattering). U.S. Pat. Nos. 4,661,913, 4,284412 and 3,826,364 and an article by Herzenberg et al., Sci. Amer., 234:108 (1976) generally describe the principles of flow cytometry. Becton Dickinson Immunocytometry Systems (BDIS) makes several flow cytometers and associated software and hardware, including FACScan TM brand flow cytometer and CONSORT 30 TM data management system, which may be used to detect and count fluorescently labelled cells. Other means for detection of fluorescently labelled cells include a fluorescent light microscope.

It will be appreciated by those skilled in the art that the improved lysing solution will reduce non-specific binding of labelled material regardless of whether one or more fluorochrome-monoclonal antibody conjugates are used.

Desirably, the lysing solution comprises a short chain aliphatic aldehyde with a carbon chain length of one to four, an alkali or alkaline earth metal salt of a weak acid, a polyhydric alcohol and one polyanion.

In the preferred embodiment of this aspect of the invention, the aldehyde is formaldehyde and is present at a final concentration of about 0.5 to 4 percent by volume; the salt is sodium citrate at a final concentration of about 0.1 to 1 percent by volume; the polyhydric alcohol is diethylene glycol at a final concentration of about 1 to 6 percent, and one polyanion is used at a final concentration of about 4 to 32 ug per ml of solution. It is desirable to use 37% formaldehyde (reagent grade), 25% sodium citrate and glass distilled water as a diluent in making the improved lysing solution. Further, it is desirable that the polyanion be sodium heparin at a concentration of 2 to 8 USP units per ml of lysing solution.

In the most preferred embodiment, the concentration of formaldehyde is about 1 percent, the concentration of sodium citrate is about 0.25 percent, the concentration of diethylene glycol is about 3 percent and the concentration of heparin is about 4 USP units per ml of solution.

In another embodiment of the invention, the labelled material is prepared and used in the presence of polyanions. Desirably, the labelled material comprises a fluorochrome conjugated to a monoclonal antibody. The polyanions may be added to the labelled material during the conjugation process, such as the conjugation process described in U.S. Pat. No. 4,520,111, or may be added to the labelled material once conjugation is complete and before storage or during use. The concentration of polyanions in the labelled material should be approximately one to one hundred times the concentration of the specific binding pair member on a weight basis.

In the preferred embodiment of this aspect of the invention, heparin is added to a labelled material, comprising a fluorochrome-monoclonal antibody conjugate, after the conjugate has been made. Desirably, the fluorochrome is a phycobiliprotein, preferably phycoerythrin. The monoclonal antibody that is used in the conjugate will depend on the receptor to be tagged. A variety of monoclonal antibodies are available from several commercial sources, including BDIS, for the detection of cell surface antigens the presence or absence of which can be used to identify leukocyte subclasses. For example, Anti Leu 2 (BDIS) will tag CD8+ cells; Anti-Leu 3a (BDIS) will tag CD$_4$+ cells; Anti Leu 4 (BDIS) will tag CD$_3$+ cells; and HLe-1 (BDIS)

will tag $CD_{45}^+$ cells. Labelled material so prepared then may be used in the method described above to tag cells in peripheral blood.

It will be appreciated by those skilled in the art that the labelled material incorporating polyanions need not be used in conjunction with peripheral blood or with a lysing solution. For example, if whole blood is used without lysing solution, PBL may be prepared by density-dependent centrifugation prior to tagging with labelled material. Alternatively, cells in a sample may be prepared from other sources, such as bone marrow, liver, spleen, lymph node or from body fluids such as urine or cerebral-spinal fluid, and may be tagged with the appropriate labelled material. In any case, the presence of polyanions will reduce the non-specific binding of the labelled material.

The following examples will more fully point out the nature of the invention, but are not intended to limit the scope of the invention which is set forth in the claims hereto.

EXAMPLE I

Peripheral blood was obtained by venipuncture from a normal individual and collected in Vacutainer® brand collection tubes containing $EDTA(K_3)$. A 50 ul aliquot of blood was placed in another tube. 20 ul of Anti Leu M3(PE) (an anti-CD14 MAb, BDIS) were added to the tube in accordance with the manufacturer's directions. Sufficient incubation was allowed for the MAb to tag its receptor (i.e., CD14 bearing cells). After said incubation time,, 2.0 ml of lysing solution containing about 1% formaldehyde, 0.25% sodium citrate and 3% diethylene qlycol (FIG. 1A) and containing 4 USP units of heparin per ml of lysing solution (FIG. 1B) were added to the tube. The tubes were shaken gently allowed sufficient time (approximately 10 minutes) to lyse the erythrocytes. The tube was centrifuged to pellet the PBL and supernatant was aspirated off. The pellet was resuspended in phosphate buffered saline (PBS). centrifuged, aspirated and resuspended in 0.5% formaldehyde in sheath fluid. The resulting mixture was placed in a FACScan ™ flow cytometer and PE fluorescence measured on channel 2 (i.e., FL2) and recorded as gated events. Data was collected and stored using CONSORT 30 ™ research software (BDIS).

Referring to FIG. 1A, the non specific binding of Anti Leu M3 in the absence of polyanions in the lysing solution is shown in quadrant 1. Of 10,000 events examined, there were 3,067 gated events of 97.13% were found in quadrant 1 and 2.80% were found in quadrant 3.

Figure 1B:
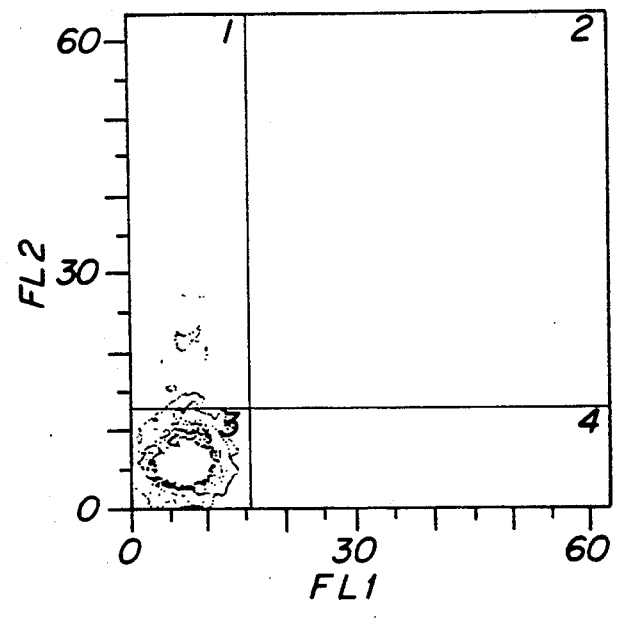

Referring to FIG. 1B, wherein the lysing solution contained a polyanion, the level of non-specific binding has decreased dramatically. Of 3,540 gated events in a 10,000 event sample, the percentage of gated events in quadrant 1 was now 3.64% and the percentage of gated events in quadrant 3 increased to 96.30%.

EXAMPLE II

The method of Example I was followed here; however, Anti HLA DR(PE) (BDIS) was used in place of Anti-Leu M3. The results are similar to Example I.

Figure 2A:
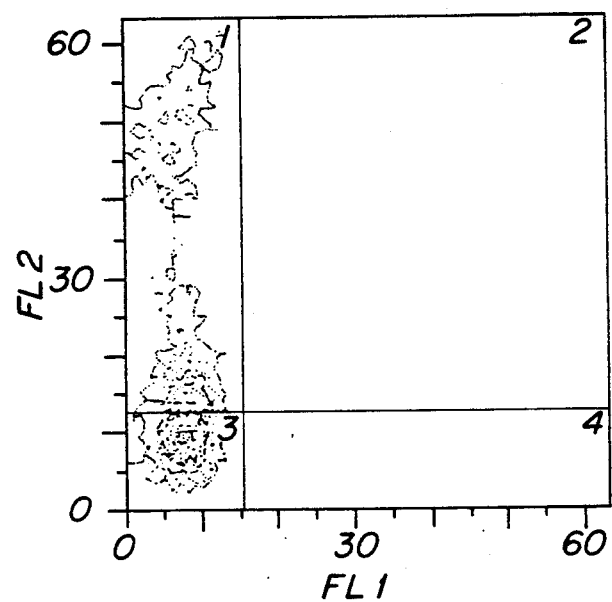
FIG. 2 comprises contour plots of fluorescence for PBL prepared as above but wherein the PBL were tagged with Anti-HLA DR(PE)
Figure 2B:
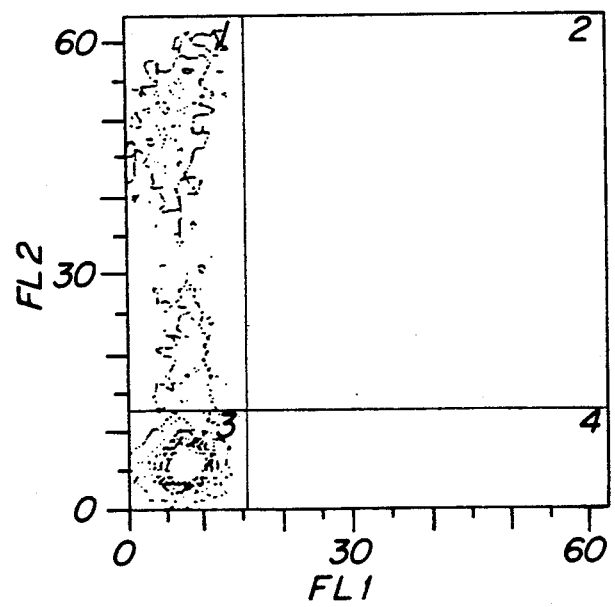

Referring to FIG. 2A, of the 2,952 gated event in a 10,000 event sample, 56.84% were found in quadrant 1 and 43.06% were found in quadrant 3. Referring to FIG. 2B, of the 3,243 gated events in a 10,000 event sample, 38.45% were found in quadrant 1 and 61.49% were found in quadrant 3 after addition of the polyanion to the lysing solution.

EXAMPLE III

Peripheral blood was prepared as in Example I; however, in place of Anti-Leu M3(PE), $IgG_{2a}$(PE) (BDIS) was used as a negative isotype control.

Figure 3A:
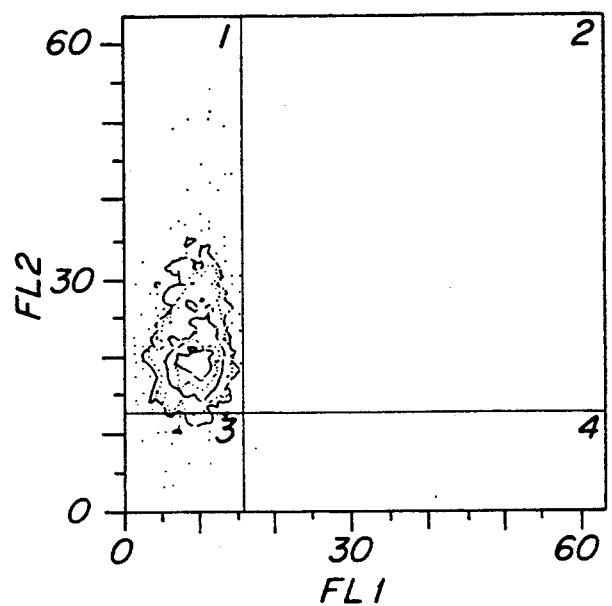
FIG. 3 comprises contour plots of fluorescence for PBL prepared as in FIG. 1 but wherein the PBL were tagged with IgG$_{2a}$(PE) as a negative control.
Figure 3B:
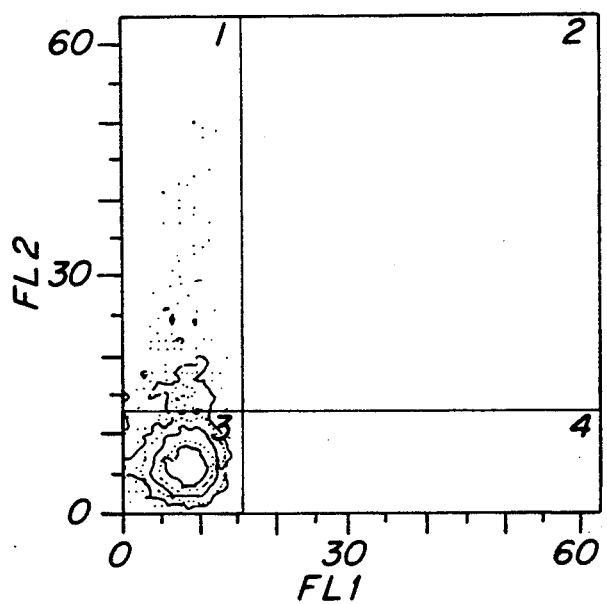

Referring to FIG. 3A, of 2,423 gated events in a 10,000 event sample, 97.77% were found in quadrant 1 and only 2.06% were found in quadrant 3. In FIG. 3B, however, the percentages nearly reverse themselves. Of 2,558 gated events in a 10,000 event sample, the percentage of gated events in quadrant 1 was decreased to 9.62% and the percentage of gated events in quadrant 3 increased to 90.34%.

In all three examples, therefore, the addition of a polyanion, such as sodium heparin, to a lysing solution caused a significant decrease in the non-specific binding of the labelled material. This surprising improvement in the level of non-specific binding increased the level of sensitivity of detection.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed:

1. In a method of identifying and enumerating non-erythrocyte cells in blood wherein an aliquot of a blood sample to be studied is provided, one or more select subclasses of non-erythrocyte cells is selectively tagged by incubating the aliquot with one or more labelled materials which are selectively reactive with distinct antigenic targets on the surface of the select subclasses, the erythrocytes in the aliquot are lysed, the aliquot is passed, substantially a cell at a time through an area of focused optical stimulation while detecting light scattered by and emitted from the cell and the cell of the selected subclass are differentiated based at least in part on comparison of the predetermined fluorescence response in the detected light, the improvement comprising utilizing a lysing agent comprising the mixture of an aqueous solution of a) a short chain aliphatic aldehyde with carbon chain length of one to four, b) an alkali or alkaline earth salt of a weak acid, c) a polyhydric alcohol, and d) one or more polyanions.

2. The method in accordance with claim 1 wherein said aldehyde is selected from the group consisting of formaldehyde and butyraldehyde.

3. The method in accordance with claim 1 wherein said alkali or alkaline earth salt of a weak acid is selected from the group consisting of sodium and potassium salts of citrate, phosphate, acetate, formate, ascorbate and bicarbonate.

4. The method in accordance with claim 1 wherein said polyhydric alcohol is selected from the group consisting of glycerol, diethylene glycol and polyethylene glycol.

5. The method in accordance with claim 1 wherein the polyanions are selected from the group consisting of sodium heparin, chondroitin sulfate, polyanethol sulfonate and pentosan polysulfate.

6. The method in accordance with claim 1 wherein said formaldehyde is present at a level of from about 0.5 to about 4 percent.

7. The method in accordance with claim 1 wherein said alkali or alkaline earth salt of a weak acid is present at a level of from about 0.1 to about 1 percent.

8. The method in accordance with claim 1 wherein said polyhydric alcohol is present at a level of from about 1 to about 6 percent.

9. The method in accordance with claim 1 wherein said polyanions are present about 4 to 32 ug per ml of lysing solution.

10. The method in accordance with claim 1 comprising a mixture of any aqueous solution of formaldehyde, diethylene qlycol, sodium citrate and sodium heparin.

11. The method in accordance with claim 10 wherein said formaldehyde is present at a level of from about 0.5 to about 4 percent, said sodium citrate is present at a level of from about 0.1 to about 1.0 percent and said diethylene qlycol is present at a level of from about 1 to about 6 percent and said sodium heparin is present at a level of about 2 to 8 USP units per ml.

12. The method in accordance with claim 11 wherein said formaldehyde is present at a level of about 1 percent, said sodium citrate is present at about 0.25 percent, said diethylene glycol is present at a level of about 3 percent and said sodium heparin is present at a level of about 4 USP units per ml.

13. A method for identification of subclasses of leukocytes in a sample of peripheral blood cells comprising:
    a) providing an aliquot from said sample;
    b) adding a labelled material to said aliquot;
    c) lysing erythrocytes in said aliquot with a lysing agent which comprises an aqueous solution of a short chain aliphatic aldehyde having a carbon chain length of from 1 to 4, an alkali or alkaline earth salt of a weak acid, a polyhydric alcohol and one or more polyanions;
    d) passing said aliquot substantially a cell at a time through an area of focused optical illumination and detecting the optical characteristics of the cells; and
    e) differentiating cells of a subclass of leukocytes at least in part on the basis of said optical characteristics.

14. A method in accordance with claim 13 wherein said aldehyde is selected from the group consisting of formaldehyde and butyraldehyde.

15. A method in accordance with claim 13 wherein said alkali or alkaline earth salt of a weak acid is selected from the group consisting of sodium and potassium salts of citrate, phosphate, acetate, formate, ascorbate and bicarbonate.

16. A method in accordance with claim 13 wherein said polyhydric alcohol is selected from the group consisting of glycerol, diethylene glycol and polyethylene glycol.

17. The method in accordance with claim 13 wherein the polyanions are selected from the group consisting of sodium heparin, chondroitin sulfate, polyanethol sulfonate and pentosan polysulfate.

18. A method in accordance with claim 13 wherein said aldehyde is present at a level of from about 0.5 to about 4 percent.

19. A method in accordance with claim 13 wherein said alkali or alkaline earth salt of a weak acid is present at a level of from about 0.1 to about 1 percent.

20. A method in accordance with claim 13 wherein said polyhydric alcohol is present at a level of from about 1 to about 6 percent.

21. The method in accordance with claim 13 wherein said polyanion is present at about 4 to 32 ug per ml of lysing solution.

22. A method in accordance with claim 13 comprising a mixture of an aqueous solution of formaldehyde, diethylene glycol, sodium citrate and sodium heparin.

23. A method in accordance with claim 22 wherein said formaldehyde is present at a level of from about 0.5 to about 44 percent, said sodium citrate is present at a level of from about 0.1 to about 1.0 percent and said diethylene glycol is present at a level of from about 1 to about 6 percent and said sodium heparin is present at a level of about 2 to 8 USP units per ml.

24. A method in accordance with claim 23 wherein said formaldehyde is present at a level of about 1 percent, said sodium citrate is present at about 0.25 percent, said diethylene qlycol is present at a level of about 3 percent and said sodium heparin is present at a level of about 4 USP units per ml.

25. A method for identification of cells in a sample comprising;
    a) providing an aliquot from said sample;
    b) adding a labelled material containing one or more polyanions to said aliquot;
    c) passing said aliquot substantially one cell at a time through an area of focused optical illumination and detecting fluorescence and light scattered by the cells; and
    d) differentiating cells in the sample at least in part on the basis of fluorescence and light scatter.

26. The method in accordance with claim 25 wherein the labelled material comprises a fluorochrome conjugated to a specific binding pair member.

27. The method in accordance with claim 26 wherein the fluorochrome is a phycobiliprotein.

28. The method in accordance with claim 27 wherein the phycobiliprotein is phycoerythrin.

29. The method in accordance with claim 26 wherein the specific binding pair member is a monoclonal antibody.

30. The method in accordance with claim 25 wherein the sample of cells is taken from peripheral blood.

31. The method in accordance with claim 30 wherein erythrocytes in the aliquot are lysed with a lysing solution containing one or more polyanions.

32. The method in accordance with claim 31 wherein the polyanions are selected from the group consisting of sodium heparin, chondroitin sulfate, polyanethol sulfonate and pentosan polysulfate.

33. The method in accordance with claim 31 wherein said lysing solution comprises a mixture of an aqueous solution of formaldehyde, diethylene glycol, sodium citrate and sodium heparin.

34. The method in accordance with claim 31 wherein polyanions are omitted from the labelled material.

35. A solution of labelled material importing reduced non-specific binding of said labelled material which comprises a mixture of an aqueous solution of:
    a) a fluorochrome conjugated to a specific binding pair member, and
    b) one or more polyanions.

36. The material in accordance with claim 35 wherein said fluorochrome is a phycobiliprotein.

37. The material in accordance with claim 36 wherein said phycobiliprotein is a phycoerythrin.

38. The material in accordance with claim 35 wherein said specific binding pair member is a ligand.

39. The material in accordance with claim 38 wherein the ligand is a monoclonal antibody.

40. An erythrocyte lysing solution which reduces non-specific binding which comprises a mixture of an aqueous solution of:
   a) a short chain aliphatic aldehyde with a carbon chain length of one to four;
   b) an alkali or alkaline earth salt of a weak acid,
   c) a polyhydric alcohol, and
   d) one or more polyanions.

41. The solution in accordance with claim 40 wherein said aldehyde is selected from the group consisting of formaldehyde and butyraldehyde.

42. The solution in accordance with claim 40 wherein said alkali or alkaline earth salt of a weak acid is selected from the group consisting of sodium and potassium salts of citrate, phosphate, acetate, formate, ascorbate and bicarbonate.

43. The solution in accordance with claim 40 wherein said polyhydric alcohol is selected from the group consisting of glycerol, diethylene glycol and polyethylene glycol.

44. The solution in accordance with claim 40 wherein the polyanions are selected from the group consisting of sodium heparin, chondroitin sulfate, polyanethol sulfonate and pentosan polysulfate.

45. The solution in accordance with claim 40 wherein said formaldehyde is present at a level of from about 0.5 to about 4 percent.

46. The solution in accordance with claim 40 wherein said alkali or alkaline earth salt of a weak acid is present at a level of from about 0.1 to about 1 percent.

47. The solution in accordance with claim 40 wherein said polyhydric alcohol is present at a level of from about 1 to about 6 percent.

48. The solution in accordance with claim 40 wherein said polyanions present about 4 to 32 ug per ml of lysing solution.

49. The solution in accordance with claim 40 comprising a mixture of an aqueous solution of formaldehyde, diethylene glycol, sodium citrate and sodium heparin.

50. The solution in accordance with claim 49 wherein said formaldehyde is present at a level of from about 0.5 to about 4 percent, said sodium citrate is present at a level of from about 0.1 to about 1.0 percent and said diethylene qlycol is present at a level of from about 1 to about 6 percent and said sodium heparin is present at a level of about 2 to 8 USP units per ml.

51. The solution in accordance with claim 50 wherein said formaldehyde is present at a level of about 1 percent, said sodium citrate is present at about 0.25 percent, said diethylene glycol is present at a level of about 3 percent and said sodium heparin is present at a level of about 4 USP units per ml.

* * * * *